US007923392B2

(12) United States Patent
Thomas

(10) Patent No.: US 7,923,392 B2
(45) Date of Patent: Apr. 12, 2011

(54) CROSSLINKED ELASTIC MATERIAL FORMED FROM A BRANCHED BLOCK COPOLYMER

(75) Inventor: Oomman P. Thomas, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 454 days.

(21) Appl. No.: 11/872,920

(22) Filed: Oct. 16, 2007

(65) Prior Publication Data
US 2009/0098787 A1 Apr. 16, 2009

(51) Int. Cl.
*D04H 1/00* (2006.01)
*B32B 5/26* (2006.01)
(52) U.S. Cl. ........ 442/328; 442/381; 442/394; 156/167; 252/8.61
(58) Field of Classification Search ............ 442/328, 442/381, 394; 156/167; 252/8.61
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,354,506 A | 11/1967 | Raley |
| 3,494,821 A | 2/1970 | Evans |
| 3,502,538 A | 3/1970 | Petersen |
| 3,502,763 A | 3/1970 | Hartmann |
| 3,542,615 A | 11/1970 | Dobo et al. |
| 3,650,649 A | 3/1972 | Schippers |
| 3,692,618 A | 9/1972 | Dorschner et al. |
| 3,801,429 A | 4/1974 | Schrenk et al. |
| 3,802,817 A | 4/1974 | Matsuki et al. |
| 3,849,241 A | 11/1974 | Butin et al. |
| 4,041,203 A | 8/1977 | Brock et al. |
| 4,070,418 A | 1/1978 | Harpell |
| 4,144,370 A | 3/1979 | Boulton |
| 4,323,534 A | 4/1982 | DesMarais |
| 4,340,563 A | 7/1982 | Appel et al. |
| 4,374,888 A | 2/1983 | Bornslaeger |
| 4,663,220 A | 5/1987 | Wisneski et al. |
| 4,704,116 A | 11/1987 | Enloe |
| 4,766,029 A | 8/1988 | Brock et al. |
| 4,789,592 A | 12/1988 | Taniguchi et al. |
| 4,795,668 A | 1/1989 | Krueger et al. |
| 4,798,603 A | 1/1989 | Meyer et al. |
| 4,834,738 A | 5/1989 | Kielpikowski et al. |
| 4,886,512 A | 12/1989 | Damico et al. |
| 4,937,299 A | 6/1990 | Ewen et al. |
| 4,965,122 A | 10/1990 | Morman |
| 4,981,747 A | 1/1991 | Morman |
| 5,003,178 A | 3/1991 | Livesay |
| 5,057,368 A | 10/1991 | Largman et al. |
| 5,069,970 A | 12/1991 | Largman et al. |
| 5,093,422 A | 3/1992 | Himes |
| 5,108,820 A | 4/1992 | Kaneko et al. |
| 5,162,074 A | 11/1992 | Hills |
| 5,169,706 A | 12/1992 | Collier, IV et al. |
| 5,176,668 A | 1/1993 | Bernardin |
| 5,176,672 A | 1/1993 | Bruemmer et al. |
| 5,192,606 A | 3/1993 | Proxmire et al. |
| 5,213,881 A | 5/1993 | Timmons et al. |
| 5,218,071 A | 6/1993 | Tsutsui et al. |
| 5,226,992 A | 7/1993 | Morman |
| 5,272,236 A | 12/1993 | Lai et al. |
| 5,277,976 A | 1/1994 | Hogle et al. |
| 5,278,272 A | 1/1994 | Lai et al. |
| 5,284,703 A | 2/1994 | Everhart et al. |
| 5,304,599 A | 4/1994 | Himes |
| 5,322,728 A | 6/1994 | Davey et al. |
| 5,332,613 A | 7/1994 | Taylor et al. |
| 5,336,545 A | 8/1994 | Morman |
| 5,336,552 A | 8/1994 | Strack et al. |
| 5,382,400 A | 1/1995 | Pike et al. |
| 5,385,775 A | 1/1995 | Wright |
| 5,399,219 A | 3/1995 | Roessler et al. |
| 5,464,688 A | 11/1995 | Timmons et al. |
| 5,466,410 A | 11/1995 | Hills |
| 5,472,775 A | 12/1995 | Obijeski et al. |
| 5,486,166 A | 1/1996 | Bishop et al. |
| 5,490,846 A | 2/1996 | Ellis et al. |
| 5,509,915 A | 4/1996 | Hanson et al. |
| 5,539,056 A | 7/1996 | Yang et al. |
| 5,540,796 A | 7/1996 | Fries |
| 5,558,659 A | 9/1996 | Sherrod et al. |

(Continued)

FOREIGN PATENT DOCUMENTS

| | | |
|---|---|---|
| WO | WO 9516425 A1 | 6/1995 |
| WO | WO 9516425 A2 | 6/1995 |
| WO | WO 9821279 A1 | 5/1998 |
| WO | WO0119918 A1 | 3/2001 |
| WO | WO 2006 074819 A1 | 7/2006 |
| WO | WO2006071321 A1 | 7/2006 |

OTHER PUBLICATIONS

Search Report and Written Opinion for PCT/IB2008/052932 dated Apr. 6, 2009.
Article—*Steady Flow and Dynamic Viscosity of Branched Butadiene-Styrene Block Copolymers*, Kraus et al., Journal of Polymer Science: Part A-2, vol. 9, 1971, pp. 1839-1850.
ASTM Designation: D 1238-01 entitled *Standard Test Method for Melt Flow Rates of Thermoplastics by Extrusion Plastometer*, Aug. 10, 2001, 12 pages.

(Continued)

*Primary Examiner* — Norca L Torres-Velazquez
(74) *Attorney, Agent, or Firm* — Dority & Manning, P.A.

(57) ABSTRACT

An elastic material for use in an absorbent article is provided. The elastic material contains a crosslinked network formed from a branched block copolymer having a monoalkenyl aromatic midblock positioned between conjugated diene endblocks (e.g., butadiene-styrene-butadiene ("B-S-B") triblock copolymer). Prior to crosslinking, the branched block copolymers have a relatively low viscosity and thus may be readily formed into a precursor elastic material (e.g., film, strands, web, etc.) that is subsequently crosslinked to achieve the desired elastic and mechanical properties. Crosslinking is typically achieved through the formation of free radicals (unpaired electrons) that link together to form a plurality of carbon-carbon covalent bonds at the conjugated diene endblocks.

24 Claims, 2 Drawing Sheets

U.S. PATENT DOCUMENTS

| | | | |
|---|---|---|---|
| 5,571,619 | A | 11/1996 | McAlpin et al. |
| 5,595,618 | A | 1/1997 | Fries et al. |
| 5,596,052 | A | 1/1997 | Resconi et al. |
| 5,649,916 | A | 7/1997 | DiPalma et al. |
| 5,718,752 | A | 2/1998 | Kluttz |
| 5,863,978 | A | 1/1999 | Vosters |
| 5,888,615 | A | 3/1999 | Mascarenhas et al. |
| 5,932,497 | A | 8/1999 | Morman et al. |
| 5,962,995 | A | 10/1999 | Avnery |
| 5,997,981 | A | 12/1999 | McCormack et al. |
| 6,015,764 | A | 1/2000 | McCormack et al. |
| 6,090,325 | A | 7/2000 | Wheat et al. |
| 6,110,158 | A | 8/2000 | Kielpikowski |
| 6,111,163 | A | 8/2000 | McCormack et al. |
| 6,200,669 | B1 | 3/2001 | Marmon et al. |
| 6,235,847 | B1 | 5/2001 | Hoshi et al. |
| 6,265,486 | B1 | 7/2001 | Shaffer et al. |
| 6,315,864 | B2 | 11/2001 | Anderson et al. |
| 6,407,492 | B1 | 6/2002 | Avnery et al. |
| 6,461,457 | B1 | 10/2002 | Taylor et al. |
| 6,500,563 | B1 | 12/2002 | Datta et al. |
| 6,511,465 | B1 | 1/2003 | Freiburger et al. |
| 6,555,624 | B2 | 4/2003 | Nishihara et al. |
| 6,632,890 | B1 | 10/2003 | Bates et al. |
| 6,663,611 | B2 | 12/2003 | Blaney et al. |
| 6,680,423 | B1 | 1/2004 | Tanzer |
| 6,730,637 | B1 | 5/2004 | Stewart et al. |
| 6,824,734 | B2 | 11/2004 | Boggs et al. |
| 6,888,044 | B2 | 5/2005 | Fell et al. |
| 7,064,164 | B2 | 6/2006 | Knoll et al. |
| 7,166,679 | B2 | 1/2007 | Willis et al. |
| 7,169,850 | B2 | 1/2007 | Handlin, Jr. et al. |
| 7,470,746 | B2 | 12/2008 | Knoll et al. |
| 2003/0068951 | A1 | 4/2003 | Boggs et al. |
| 2003/0181584 | A1* | 9/2003 | Handlin et al. ............... 525/88 |
| 2004/0006324 | A1 | 1/2004 | Zhou et al. |
| 2004/0060112 | A1 | 4/2004 | Fell et al. |
| 2004/0110442 | A1 | 6/2004 | Rhim et al. |
| 2004/0121687 | A1 | 6/2004 | Morman et al. |
| 2004/0260021 | A1* | 12/2004 | Macedo et al. ............... 525/63 |
| 2005/0170729 | A1 | 8/2005 | Stadelman et al. |
| 2005/0245162 | A1 | 11/2005 | McCormack et al. |
| 2005/0248051 | A1 | 11/2005 | Cancio et al. |
| 2005/0256264 | A1 | 11/2005 | Suzuki et al. |
| 2006/0079617 | A1 | 4/2006 | Kappes et al. |
| 2006/0135024 | A1 | 6/2006 | Thomas et al. |
| 2006/0151914 | A1 | 7/2006 | Gerndt et al. |
| 2006/0246803 | A1 | 11/2006 | Smith et al. |
| 2007/0068233 | A1 | 3/2007 | Lewtas et al. |

OTHER PUBLICATIONS

ASTM Designation: D 5035-95 entitled *Standard Test Method for Breaking Force and Elongation of Textile Fabrics (Strip Method)*, May 15, 1995, pp. 682-688.

N. R. Legge et al. "Thermoplastic Elastomers: A comprehensive Review" Oxford University Press, 1987: 54-63, 75-78.

*Matrix Chain Deformation in Reinforced Networks: a SANS Approach*, Westermann et al., Macromolecules, vol. 32, No. 18, 1999, pp. 5793-5802.

* cited by examiner

CROSSLINKED ELASTIC MATERIAL FORMED FROM A BRANCHED BLOCK COPOLYMER

BACKGROUND OF THE INVENTION

Elastic films are commonly incorporated into products (e.g., diapers, training pants, garments, etc.) to improve their ability to better fit the contours of the body. For example, an elastic composite may be formed from the elastic film and one or more nonwoven web facings. The nonwoven web facing may be joined to the elastic film while the film is in a stretched condition so that the nonwoven web facing can gather between the locations where it is bonded to the film when it is relaxed. The resulting elastic composite is stretchable to the extent that the nonwoven web facing gathered between the bond locations allows the elastic film to elongate. Styrenic block copolymers are often employed to form the elastic film of such composites that contain a conjugated butadiene block positioned between two styrene blocks (i.e., S-B-S). Unfortunately, such polymers are often difficult to process into a film due to their relatively high viscosity. As such, a need exists for a material that may be formed from a low viscosity polymer, yet exhibit good elastic performance during use.

SUMMARY OF THE INVENTION

In accordance with one embodiment of the present invention, a nonwoven web material is disclosed that comprises an elastic component that includes a crosslinked network containing a branched block copolymer having a monoalkenyl aromatic midblock positioned between conjugated diene endblocks.

In accordance with another embodiment of the present invention, a method for forming a nonwoven composite is disclosed. The method comprises melt extruding a branched block copolymer having a monoalkenyl aromatic midblock positioned between conjugated diene endblocks; forming a precursor elastic material from the melt extruded copolymer; laminating the precursor elastic material to a nonwoven web facing; and crosslinking the branched block copolymer.

In accordance with still another embodiment of the present invention, an elastic material is disclosed that comprises a crosslinked network. The crosslinked network contains a branched block copolymer having a monoalkenyl aromatic midblock positioned between conjugated diene endblocks, wherein the monoalkenyl aromatic midblock constitutes from about 1 wt. % to about 40 wt. % of the copolymer.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
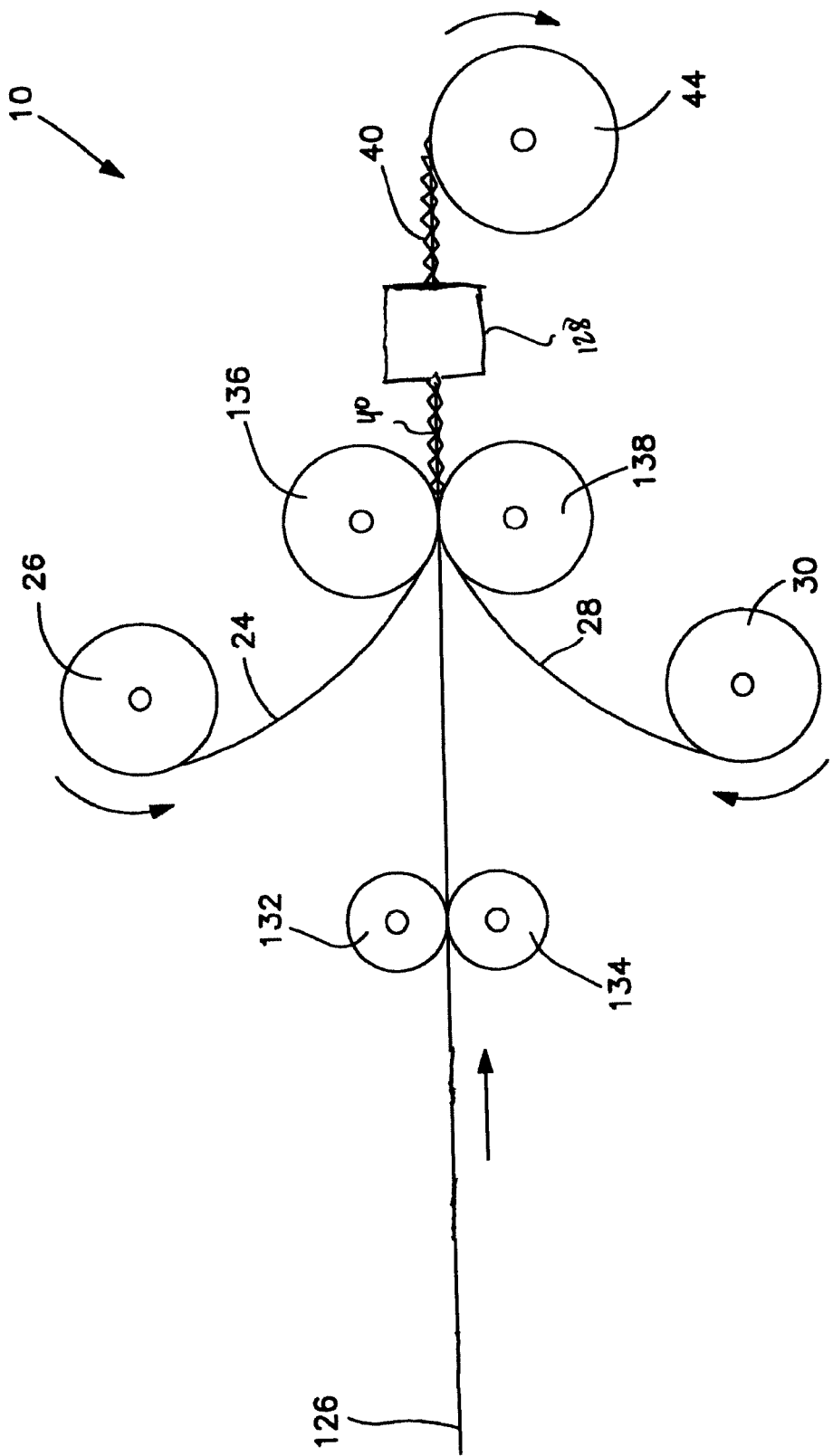
FIG. 1 is a schematic illustration of a method for forming a composite in accordance with one embodiment of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art.

As used herein, the term "nonwoven web" generally refers to a web having a structure of individual fibers or threads which are interlaid, but not in an identifiable manner as in a knitted fabric. Examples of suitable nonwoven fabrics or webs include, but are not limited to, meltblown webs, spunbond webs, carded webs, etc. The basis weight of the nonwoven web may generally vary, such as from about 0.1 grams per square meter ("gsm") to 120 gsm, in some embodiments from about 0.5 gsm to about 70 gsm, and in some embodiments, from about 1 gsm to about 35 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. Nos. 4,340,563 to Appel, et al., 3,692,618 to Dorschner, et al., 3,802,817 to Matsuki, et al., 3,338,992 to Kinney, 3,341,394 to Kinney, 3,502,763 to Hartman, 3,502,538 to Levy, 3,542,615 to Dobo, et al., and 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

As used herein, the terms "machine direction" or "MD" generally refers to the direction in which a material is produced. The term "cross-machine direction" or "CD" refers to the direction perpendicular to the machine direction. Dimensions measured in the cross-machine direction are referred to as "width" dimension, while dimensions measured in the machine direction are referred to as "length" dimensions.

As used herein, the term "elastomeric" and "elastic" and refers to a material that, upon application of a stretching force, is stretchable in a direction (such as the MD or CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a 2.54-cm sample of a material that is stretchable to at least 3.81 centimeters and which, upon release of the stretching force, will recover to a length of not more than 3.175 centimeters. Desirably, the material contracts or recovers at least 50%, and even more desirably, at least 80% of the stretched length.

As used herein the terms "extensible" or "extensibility" generally refers to a material that stretches or extends in the direction of an applied force by at least about 50% of its relaxed length or width. An extensible material does not necessarily have recovery properties. For example, an elastomeric material is an extensible material having recovery properties. A meltblown web may be extensible, but not have recovery properties, and thus, be an extensible, non-elastic material.

As used herein, the term "percent stretch" refers to the degree to which a material stretches in a given direction when subjected to a certain force. In particular, percent stretch is determined by measuring the increase in length of the material in the stretched dimension, dividing that value by the original dimension of the material, and then multiplying by 100. Such measurements are determined using the "strip elongation test", which is substantially in accordance with the specifications of ASTM D5035-95. Specifically, the test uses two clamps, each having two jaws with each jaw having a facing in contact with the sample. The clamps hold the material in the same plane, usually vertically, separated by 3 inches (7.62 cm) and move apart at a specified rate of extension. The sample size is 3 inches by 6 inches (7.62 cm×15.24 cm), with a jaw facing height of 1 inch (2.54 cm) and width of 3 inches (7.62 cm), and a constant rate of extension of 300 mm/min. The specimen is clamped in, for example, a Sintech 2/S tester with a Renew MTS mongoose box (control) and using TESTWORKS 4.07b software (MTS Corp, of Minneapolis, Minn.). The test is conducted under ambient conditions. Results are generally reported as an average of three specimens and may be performed with the specimen in the cross direction (CD) and/or the machine direction (MD).

As used herein, a "branched" polymer generally refers to a polymer that contains a long chain backbone to which is attached side chains. The branched polymer may possess any desired configuration, such as star, comb, dendritic, etc. Star-shaped branched polymers, for instance, contain side chains that extend outwardly (e.g., radially) from a branch point.

Detailed Description

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to an elastic material for use in an absorbent article. The elastic material contains a crosslinked network formed from a branched block copolymer having a monoalkenyl aromatic midblock positioned between conjugated diene endblocks (e.g., triblock). Exemplary copolymers may include, for instance, B-S-B triblock copolymers, I-S-I triblock copolymers, and so forth. Such branched block copolymers may be formed using any known technique, such as sequential polymerization or through coupling, which may leave a residue of the coupling agent in the polymer. Regardless, prior to crosslinking, the branched block copolymers have a relatively low viscosity and thus may be readily formed into a precursor elastic material (e.g., film, strands, web, etc.) that is subsequently crosslinked to achieve the desired elastic and mechanical properties. Crosslinking is typically achieved through the formation of free radicals (unpaired electrons) that link together to form a plurality of carbon-carbon covalent bonds at the conjugated diene endblocks. The use of multiple conjugated diene endblocks in the copolymer of the present invention thus provides a greater number of crosslinking sites than would otherwise be available if, for example, the conjugated diene was a midblock of the copolymer (e.g., S-B-S copolymers). Because the copolymer is branched, an even greater number of available crosslinking sites may be provided. Further, a greater portion of the styrene blocks may be contained within the crosslinked network so that it contains fewer "dangling" styrene chains than conventional S-B-S block copolymers. This is desirable because the larger dangling styrene blocks can sterically hinder crosslinking at the conjugated diene sites, thereby reducing elasticity. Thus, by possessing a greater number of crosslinking sites and fewer "dangling" styrene chains, the resulting three-dimensional network may likewise possess enhanced strength and elasticity.

The monoalkenyl aromatic midblock may include styrene, as well as derivatives thereof, such as α-methylstyrene, p-methylstyrene, p-tert-butyl styrene, p-ethylstyrene, m-isopropylstyrene, p-hexylstyrene, α-methylstyrene, α,4-dimethylstyrene, 1,3 dimethylstyrene p-methylstyrene; etc., as well as other monoalkenyl polycyclic aromatic compounds, such as vinyl naphthalene, vinyl anthrycene; and so forth. Preferred monoalkenyl aromatics are styrene and p-methylstyrene. The conjugated diene endblocks may include homopolymers of conjugated diene monomers, copolymers of two or more conjugated dienes, and copolymers of one or more of the dienes with another monomer in which the blocks are predominantly conjugated diene units. Preferably, the conjugated dienes contain from 4 to 8 carbon atoms, such as 1,3 butadiene(butadiene), 2-methyl-1,3 butadiene(isoprene), 2,3 dimethyl-1,3 butadiene, 1,3 pentadiene(piperylene), 1,3 hexadiene, 2-methyl-1,3-hexadiene, 1,3-octadiene, or derivatives thereof. Of the conjugated dienes, butadiene and isoprene are preferred.

Any known polymerization technique may be employed to form the branched block copolymers, such as sequential addition of monomer techniques, incremental addition of monomer techniques, coupling techniques, and so forth. Exemplary techniques are described, for instance, in U.S. Pat. Nos. 4,070,418 to Harnell; 5,863,978 to Vosters; and 6,730,637 to Stewart, et al., all of which are incorporated herein in their entirety by reference thereto for all purposes. In one particular embodiment, the block copolymer is produced by sequential polymerization. By way of example, a conjugated diene monomer may be initially polymerized using 1,2-polymerization or 1,4-polymerization. In 1,2-polymerization, one carbon-carbon double bond of the conjugated diene is involved in the formation of the polymer chain, which then has pendant ethylenically unsaturated groups. In 1,4-polymerization, both carbon-carbon double bonds are involved in the formation of the polymeric chain, which then includes ethylenic unsaturation. The term "vinyl content" refers to the fact that a conjugated diene is polymerized via 1,2-addition (in the case of butadiene—it would be 3,4-addition in the case of isoprene). Although a pure "vinyl" group is formed only in the case of 1,2-addition polymerization of 1,3-butadiene, the effects of 3,4-addition polymerization of isoprene (and similar addition for other conjugated dienes) on the final properties of the block copolymer will be similar. The term "vinyl" refers to the presence of a pendant vinyl group on the polymer chain. When referring to the use of butadiene as the conjugated diene, it is preferred that about 5 to about 25 mol percent of the condensed butadiene units in the conjugated diene polymer block have 1,2 vinyl configuration as determined by proton NMR analysis.

Regardless, a monoalkenyl aromatic block is allowed to "grow" on the initial block of the polymerized conjugated diene. Substantially complete polymerization of the conjugated diene before the polymerization of monoalkenyl aromatic results in the production of rather discrete blocks. The product of the conjugated diene polymerization is contacted, for example, with additional conjugated diene to grow a second block of polymerized conjugated diene and produce a living polymer of these three blocks ("triblock copolymer"). Additional blocks may be introduced, if desired, by continuing the sequence. Subsequently, the living block polymer is contacted with an active hydrogen compound (e.g., acid or an alcohol) to "kill" the living polymer and thereby terminate polymerization. Coupling agents of higher functionality may help produce block copolymers of a branched configuration. For example, the use of a polyvinylaromatic coupling agent (e.g., divinylbenzene) may result in block copolymers of a "star" configuration.

A variety of characteristics of the branched block copolymer may be selectively varied to achieve the desired properties of the elastic material. For example, the block copolymer may possess a molecular weight within an optimum range for processing. Namely, polymers having too great of a molecular weight generally possess heavily entangled polymer chains and thus result in a thermoplastic composition that is difficult to process. Conversely, polymers having too low of a molecular weight do not generally possess enough entanglement, which leads to a relatively weak melt strength. Thus, the block copolymer is typically formed to have a number average molecular weight ("$M_n$") ranging from about 30,000 to about 150,000 grams per mole, in some embodiments from about 40,000 to about 125,000 grams per mole, in some embodiments from about 50,000 to about 110,000 grams per mole, and in some embodiments, from about 70,000 to about 110,000 grams per mole. The number average molecular weight may be determined by methods known to those skilled in the art. The molecular weight of each block may also be controlled to influence the rheology, molecular weight, and thermal properties of the copolymer. Monoalkenyl aromatic blocks with a lower molecular weight, for instance, may result in copolymers with lower softening/melting points and molecular weights. However, too low of a molecular weight may adversely affect the strength of the resulting elastic material. Thus, each monoalkenyl aromatic block employed in the copolymer may have a number average molecular weight ("$M_n$") of from about 5,000 to about 35,000 grams per mole, in some embodiments from about 7,500 to about 30,000 grams per mole, and in some embodiments, from about 10,000 to about 25,000 grams per mole. Likewise, each conjugated diene block employed in the copolymer may have a number average molecular weight ("$M_n$") ranging from about 20,000 to about 150,000 grams per mole, in some embodiments from about 30,000 to about 120,000 grams per mole, and in some embodiments, from about 40,000 to about 100,000 grams per mole.

The relative amount of the blocks in the copolymer may also influence the properties of the resulting elastic material. For example, higher monoalkenyl aromatic block concentrations may result in copolymers with lower melting points and molecular weights. However, too high of a monoalkenyl aromatic block concentration may not achieve the desired strength. Thus, the monoalkenyl aromatic block(s) typically constitute from about 1 wt. % to about 40 wt. %, in some embodiments from about 5 wt. % to about 35 wt. %, and in some embodiments, from about 15 wt. % to about 30 wt. % of the copolymer. Likewise, the conjugated diene blocks typically constitute from about 60 wt. % to about 99 wt. %, in some embodiments from about 65 wt. % to about 95 wt. %, and in some embodiments, from about 70 wt. % to about 85 wt. % of the copolymer.

To provide improved processability, the branched block copolymer is also formed to have a "melt flow index" within a certain range. The melt flow index is the weight of a polymer (in grams) that may be forced through an extrusion rheometer orifice (0.0825-inch diameter) when subjected to a force of 2160 grams in 10 minutes at a certain temperature (e.g., 190° C. or 230° C.). More specifically, polymers having a low melt flow index, or conversely a high viscosity, are generally difficult to process. Thus, in most embodiments, the melt flow index of the block copolymer is high enough to provide a low viscosity polymer, such as at least about 1 gram per 10 minutes, in some embodiments at least about 10 grams per 10 minutes, and in some embodiments, from about 15 to about 500 grams per 10 minutes, measured in accordance with ASTM Test Method D1238-E at 190° C. Of course, the melt flow index of the copolymer will ultimately depend upon the selected forming process.

If desired, the branched block copolymer may also be subjected to selective hydrogenation as is known in the art. More specifically, it is well known that block copolymers may be hydrogenated under conditions that hydrogenate from about 80% to about 99% of the aliphatic unsaturation present in the block copolymer, while hydrogenating no more than 25%, and preferably no more than 5%, of the aromatic unsaturation of the polymer molecule. Conditions to effect such hydrogenation, including the choice of a hydrogenation catalyst, are conventional and are well understood in the art. The resulting selectively hydrogenated block copolymers may be identified by the "apparent" structure of the aliphatic block. For example, selective hydrogenation of a butadiene-styrene-butadiene ("B-S-B") polymer will result in the production of a polymer having endblocks that are an apparent polyethylene in the case of conjugated diene blocks produced by 1,4-polymerization and an apparent ethylene/butylene copolymer in the case of conjugated diene blocks produced by predominantly 1,2-polymerization. These selectively hydrogenated block copolymers may be designated E-S-E and EB-S-EB, respectively. Likewise, the selective hydrogenation of an isoprene-styrene-isoprene ("I-S-I") block copolymer will result in the production of a polymer having endblocks that are an apparent ethylene/propylene copolymer in the case of isoprene blocks produced by predominantly 1,4-polymerization. Such hydrogenated block copolymers may be designated EP-S-EP. Similar nomenclature applies to block copolymers having more than three blocks.

Also suitable are functionalized derivatives of the above-described block copolymers. For example, suitable functional groups that may be introduced into the block copolymer molecule may include hydroxyl, epoxy, carboxyl or carboxylic acid anhydride functional groups. The introduction of such groups by further reaction of the initially produced block copolymers is conventional and well known in the art. Of the functionalized block copolymers, the preferred polymers contain carboxyl functional groups illustratively produced by reaction of the initially produced, non-functionalized block copolymer with acrylic acid, methacrylic acid or maleic acid.

The number of "arms" or side chains in the branched block copolymer of the present invention may vary as desired, such as from about 3 to about 30, and in some embodiments, from about 4 to about 8. Each arm may have a respective number average molecular weight of about 5,000 to about 30,000, while the total molecular weight of the block copolymer may still fall within the ranges noted above.

Regardless of its particular configuration, the low viscosity, monoalkenyl aromatic/conjugated diene block copolymer of the present invention is incorporated into a precursor elastic material. In contrast to conventional elastomeric block copolymers having a relatively high viscosity, the low viscosity block copolymers of the present invention may be readily processed without difficulty. The precursor elastic material may be a film, foam, strands, nonwoven web, and so forth. In one embodiment, for example, the precursor elastic material includes a film. Any known technique may be used to form a film, including blowing, casting, flat die extruding, etc. In one particular embodiment, the film may be formed by a blown process in which a gas (e.g., air) is used to expand a bubble of a melt extruded polymer through an annular die. The bubble is then collapsed and collected in flat film form. Processes for producing blown films are described, for instance, in U.S. Pat. Nos. 3,354,506 to Raley; 3,650,649 to Schippers; and 3,801,429 to Schrenk et al., as well as U.S. Patent Application Publication Nos. 2005/0245162 to McCormack, et al. and 2003/0068951 to Boggs, et al., all of which are incorporated herein in their entirety by reference thereto for all purposes. Although not required, the film may be stretched to improve its properties. For example, the film may be drawn by rolls rotating at different speeds of rotation so that the sheet is stretched to the desired draw ratio in the longitudinal direction (machine direction). In addition, the uniaxially stretched film may also be oriented in the cross-machine direction to form a "biaxially stretched" film. For example, the film may be clamped at its lateral edges by chain clips and conveyed into a tenter oven. In the tenter oven, the film may be drawn in the cross-machine direction to the desired draw ratio by chain clips diverged in their forward travel. Various parameters of a stretching operation may be selectively controlled, including the draw ratio, stretching temperature, and so forth. In some embodiments, for example, the film is stretched in the machine direction at a stretch ratio of from about 1.5 to about 7.0, in some embodiments from about 1.8 to about 5.0, and in some embodiments, from about 2.0 to about 4.5. The stretch ratio may be determined by dividing the length of the stretched film by its length before stretching. The stretch ratio may also be approximately the same as the draw ratio, which may be determined by dividing the linear speed of the film upon stretching (e.g., speed of the nip rolls) by the linear speed at which the film is formed (e.g., speed of casting rolls or blown nip rolls). The film may be stretched at a temperature from about 15° C. to about 50° C., in some embodiments from about 25° C. to about 40° C., and in some embodiments, from about 30° C. to about 40° C. Preferably, the film is "cold drawn", i.e., stretched without the application of external heat (e.g., heated rolls).

The film may be a mono- or multi-layered film. Multilayer films may be prepared by co-extrusion of the layers, extrusion coating, or by any conventional layering process. Such multilayer films normally contain a base layer and skin layer, but may contain any number of layers desired. For example, the multilayer film may be formed from a base layer and one or more skin layers, wherein the base layer is formed from a block copolymer in accordance with the present invention. In such embodiments, the skin layer(s) may be formed from any film-forming polymer. If desired, the skin layer(s) may contain a softer, lower melting polymer or polymer blend that renders the layer(s) more suitable as heat seal bonding layers for thermally bonding the film to a nonwoven web facing. In most embodiments, the skin layer(s) are formed from an olefin polymer. Additional film-forming polymers that may be suitable for use with the present invention, alone or in combination with other polymers, include ethylene vinyl acetate, ethylene ethyl acrylate, ethylene acrylic acid, ethylene methyl acrylate, ethylene normal butyl acrylate, nylon, ethylene vinyl alcohol, polystyrene, polyurethane, and so forth.

In another embodiment of the present invention, the precursor elastic material includes a plurality of strands. The number of strands may vary as desired, such as from 5 to about 20, in some embodiments from about 7 to about 18, and in some embodiments, from about 8 to 15 strands per cross-directional inch. The strands may have a circular cross-section, but may alternatively have other cross-sectional geometries such as elliptical, rectangular as in ribbon-like strands, triangular, multi-lobal, etc. The diameter of the strands (the widest cross-sectional dimension) may vary as desired, such as within a range of from 0.1 to about 4 millimeters, in some embodiments from about 0.2 to about 2.5 millimeters, and in some embodiments, from 0.5 to about 2 millimeters. Further, the strands may generally be arranged in any direction or pattern. For example, in one embodiment, the strands are arranged in a direction that is substantially parallel to the machine direction and are desirably spaced apart from each other across the cross machine direction at similar intervals. The strands may be substantially continuous in length so that they are in the form of filaments. Such filaments may be produced using any of a variety of known techniques, such as by melt extruding a polymer from a die having a series of extrusion capillaries arranged in a row. As is well known in the art, meltblown dies may be suitable for forming the filaments, except that the high velocity gas streams used in fiber attenuation are generally not employed. Rather, the molten polymer extrudate is pumped from the die capillaries and allowed to extend away from the die under the impetus of gravity.

If desired, a layer of the aforementioned strands may also be laminated to an additional layer (e.g., meltblown web) to help secure the strands to a facing so that they are less likely to loosen during use. Examples of such laminates are described in more detail, for instance, in U.S. Pat. No. 5,385,775 to Wright and U.S. Patent Application Publication No. 2005/0170729 to Stadelman, et al., which are incorporated herein in their entirety by reference thereto for all purposes. In one embodiment, the strands contain the block copolymer of the present invention and the meltblown web contains a polyolefin.

Regardless of the particular form of the precursor elastic material, the branched block copolymer of the present invention is typically employed in an amount of about 10 wt. % or more, in some embodiments about 25 wt. % or more, in some embodiments about 50 wt. % or more, in some embodiments about 75 wt. % or more, and in some embodiments, from about 75 wt. % to about 95 wt. % of the polymer content of the material. Of course, other polymers may also be employed in the elastic material. When employed, the additional polymer(s) typically constitute from about 0.5 to about 90 wt. %, in some embodiments from about 0.75 to about 75 wt. %, in some embodiments from about 1 wt. % to about 50 wt. %, in some embodiments from about 2 wt. % to about 40 wt. %, and in some embodiments, from about 5 wt. % to about 25 wt. % of the precursor elastic material.

In one embodiment, for example, an additional thermoplastic elastomer may be employed to improve the elastic performance of the resulting elastic material. Any of a variety of thermoplastic elastomers may generally be employed, such as elastomeric polyesters, elastomeric polyurethanes, elastomeric polyamides, elastomeric copolymers, and so forth. For example, the thermoplastic elastomer may be a block copolymer having blocks of a monoalkenyl arene polymer separated by a block of a conjugated diene polymer. Contrary to the block copolymers of the present invention, such block copolymers have a relatively high viscosity and are generally elastic in nature, even prior to crosslinking. Particularly suitable thermoplastic elastomers are available from Kraton Polymers LLC of Houston, Tex. under the trade name KRATON®. KRATON® polymers include styrene-diene block copolymers, such as styrene-butadiene, styrene-isoprene, styrene-butadiene-styrene, and styrene-isoprene-styrene. KRATON® polymers also include styrene-olefin block copolymers formed by selective hydrogenation of styrene-diene block copolymers. Examples of such styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. Specific KRATON® block copolymers include those sold under the brand names G 1652, G 1657, and G 1730. Various suitable styrenic block copolymers are described in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copolymers available from Dexco Polymers, LP of Houston, Tex. under the trade designation VECTOR™. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

Other exemplary thermoplastic elastomers that may be used include polyurethane elastomeric materials such as, for example, those available under the trademark ESTANE from Noveon, polyamide elastomeric materials such as, for example, those available under the trademark PEBAX (poly-ether amide) from Atofina Chemicals Inc., of Philadelphia, Pa., and polyester elastomeric materials such as, for example, those available under the trade designation HYTREL from E.I. DuPont De Nemours & Company.

Furthermore, the precursor elastic material of the present invention may also contain a polyolefin, such as polyethylene, polypropylene, blends and copolymers thereof. In one particular embodiment, a polyethylene is employed that is a copolymer of ethylene or propylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene or propylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

The density of a linear olefin copolymer is a function of both the length and amount of the α-olefin. That is, the greater the length of the α-olefin and the greater the amount of α-olefin present, the lower the density of the copolymer. Although not necessarily required, linear "plastomers" are particularly desirable in that the content of α-olefin short chain branching content is such that the copolymer exhibits both plastic and elastomeric characteristics—i.e., a "plastomer." Because polymerization with α-olefin comonomers decreases crystallinity and density, the resulting plastomer normally has a density lower than that of thermoplastic polymers (e.g., LLDPE), but approaching and/or overlapping that of an elastomer. For example, the density of the plastomer may be about 0.91 grams per cubic centimeter (g/cm$^3$) or less, in some embodiments from about 0.85 to about 0.89 g/cm$^3$, and in some embodiments, from about 0.85 g/cm$^3$ to about 0.88 g/cm$^3$. Despite having a density similar to elastomers, plastomers generally exhibit a higher degree of crystallinity, are relatively non-tacky, and may be formed into pellets that are non-adhesive and relatively free flowing.

Any of a variety of known techniques may generally be employed to form such polyolefins. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. Nos. 5,571,619 to McAlpin et al.; 5,322,728 to Davis et al.; 5,472,775 to Obijeski et al.; 5,272,236 to Lai et al.; and 6,090,325 to Wheat, et al., which are incorporated herein in their entirety by reference thereto for all purposes.

Particularly suitable plastomers for use in the present invention may include ethylene-based copolymer plastomers available under the EXACT™ from ExxonMobil Chemical Company of Houston, Tex. Other suitable polyethylene plastomers are available under the designation ENGAGE™ and AFFINITY™ from Dow Chemical Company of Midland, Mich. Still other suitable ethylene polymers are available from The Dow Chemical Company under the designations DOWLEX™ (LLDPE) and ATTANE™ (ULDPE). Other suitable ethylene polymers are described in U.S. Pat. Nos. 4,937,299 to Ewen et al.; 5,218,071 to Tsutsui et al.; 5,272,236 to Lai, et al.; and 5,278,272 to Lai, et al., which are incorporated herein in their entirety by reference thereto for all purposes. Suitable propylene-based plastomers are likewise commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Datta, et al.; U.S. Pat. No. 5,539,056 to Yang, et al.; and U.S. Pat. No. 5,596,052 to Resconi, et al., which are incorporated herein in their entirety by reference thereto for all purposes.

Besides polymers, the precursor elastic material of the present invention may also contain other components as is known in the art. In one embodiment, for example, the film contains a filler. Fillers are particulates or other forms of material that may be added to the film polymer extrusion blend and that will not chemically interfere with the extruded film, but which may be uniformly dispersed throughout the film. Fillers may serve a variety of purposes, including enhancing film opacity and/or breathability (i.e., vapor-permeable and substantially liquid-impermeable). For instance, filled films may be made breathable by stretching, which causes the polymer to break away from the filler and create microporous passageways. Breathable microporous elastic films are described, for example, in U.S. Pat. Nos. 5,997,981; 6,015,764; and 6,111,163 to McCormack, et al.; 5,932,497 to Morman, et al.; 6,461,457 to Taylor, et al., which are incorporated herein in their entirety by reference thereto for all purposes.

The fillers may have a spherical or non-spherical shape with average particle sizes in the range of from about 0.1 to about 7 microns. Examples of suitable fillers include, but are not limited to, calcium carbonate, various kinds of clay, silica, alumina, barium carbonate, sodium carbonate, magnesium carbonate, talc, barium sulfate, magnesium sulfate, aluminum sulfate, titanium dioxide, zeolites, cellulose-type powders, kaolin, mica, carbon, calcium oxide, magnesium oxide, aluminum hydroxide, pulp powder, wood powder, cellulose derivatives, chitin and chitin derivatives. A suitable coating, such as stearic acid, may also be applied to the filler particles if desired. When utilized, the filler content may vary, such as from about 25 wt. % to about 75 wt. %, in some embodiments, from about 30 wt. % to about 70 wt. %, and in some embodiments, from about 40 wt. % to about 60 wt. % of the film.

Other additives may also be incorporated into the precursor elastic material, such as crosslinking catalysts, pro-rad additives, melt stabilizers, processing stabilizers, heat stabilizers, light stabilizers, antioxidants, heat aging stabilizers, whitening agents, antiblocking agents, bonding agents, tackifiers, viscosity modifiers, etc. Suitable crosslinking catalysts, for instance, may include organic bases, carboxylic acids, and organometallic compounds, such as organic titanates and complexes or carboxylates of lead, cobalt, iron, nickel, zinc and tin (e.g., dibutyltindilaurate, dioctyltinmaleate, dibutyltindiacetate, dibutyltindioctoate, stannous acetate, stannous octoate, lead naphthenate, zinc caprylate, cobalt naphthenate; etc.). Suitable pro-rad additives may likewise include azo compounds, organic peroxides and polyfunctional vinyl or allyl compounds such as, triallyl cyanurate, triallyl isocyanurate, pentaerthritol tetramethacrylate, glutaraldehyde, polyester acrylate oligomers (e.g., available from Sartomer under the designation CN2303), ethylene glycol dimethacrylate, diallyl maleate, dipropargyl maleate, dipropargyl monoallyl cyanurate, dicumyl peroxide, di-tert-butyl peroxide, t-butyl perbenzoate, benzoyl peroxide, cumene hydroperoxide, t-butyl peroctoate, methyl ethyl ketone peroxide, 2,5-dimethyl-2, 5-di(t-butyl peroxy)hexane, lauryl peroxide, tert-butyl peracetate, azobisisobutyl nitrite, etc.

Examples of suitable tackifiers may include, for instance, hydrogenated hydrocarbon resins. REGALREZ™ hydrocarbon resins are examples of such hydrogenated hydrocarbon resins, and are available from Eastman Chemical. Other tackifiers are available from ExxonMobil under the ESCOREZ™ designation. Viscosity modifiers may also be employed, such as polyethylene wax (e.g., EPOLENE™ C-10 from Eastman Chemical). Phosphite stabilizers (e.g., IRGAFOS available from Ciba Specialty Chemicals of Terrytown, N.Y. and DOVERPHOS available from Dover Chemical Corp. of Dover, Ohio) are exemplary melt stabilizers. In addition, hindered amine stabilizers (e.g., CHIMASSORB available from Ciba Specialty Chemicals) are exemplary heat and light stabilizers. Further, hindered phenols are commonly used as an antioxidant in the production of films. Some suitable hindered phenols include those available from Ciba Specialty Chemicals of under the trade name "Irganox®", such as Irganox® 1076, 1010, or E 201. Moreover, bonding agents may also be added to the film to facilitate bonding to additional materials (e.g., nonwoven web). When employed, such additives (e.g., tackifier, antioxidant, stabilizer, crosslinking agents, pro-rad additives, etc.) may each be present in an amount from about 0.001 wt. % to about 25 wt. %, in some embodiments, from about 0.005 wt. % to about 20 wt. %, and in some embodiments, from 0.01 wt. % to about 15 wt. % of the elastic material.

In accordance with the present invention, the branched block copolymer is crosslinked after it is incorporated into the precursor elastic material to provide the polymer and material with elastic characteristics. Crosslinking may be achieved through the formation of free radicals (unpaired electrons) that link together to form a plurality of carbon-carbon covalent bonds. Free radical formation may be accomplished in a variety of ways, such as through electromagnetic radiation, either alone or in the presence of pro-rad additives, such as described above. More specifically, crosslinking may be induced by subjecting the precursor elastic material to electromagnetic radiation. Some suitable examples of electromagnetic radiation that may be used in the present invention include, but are not limited to, ultraviolet light, electron beam radiation, natural and artificial radio isotopes (e.g., $\alpha$, $\beta$, and $\gamma$ rays), x-rays, neutron beams, positively-charged beams, laser beams, and so forth. Electron beam radiation, for instance, involves the production of accelerated electrons by an electron beam device. Electron beam devices are generally well known in the art. For instance, in one embodiment, an electron beam device may be used that is available from Energy Sciences, Inc., of Woburn, Mass. under the name "Microbeam LV." Other examples of suitable electron beam devices are described in U.S. Pat. Nos. 5,003,178 to Livesay; 5,962,995 to Avnery; 6,407,492 to Avnery, et al., which are incorporated herein in their entirety by reference thereto for all purposes.

When supplying electromagnetic radiation, it is generally desired to selectively control various parameters of the radiation to enhance the degree of crosslinking. For example, one parameter that may be controlled is the wavelength $\lambda$ of the electromagnetic radiation. Specifically, the wavelength $\lambda$ of the electromagnetic radiation varies for different types of radiation of the electromagnetic radiation spectrum. Although not required, the wavelength $\lambda$ of the electromagnetic radiation used in the present invention is generally about 1000 nanometers or less, in some embodiments about 100 nanometers or less, and in some embodiments, about 1 nanometer or less. Electron beam radiation, for instance, typically has a wavelength λ of about 1 nanometer or less. Besides selecting the particular wavelength λ of the electromagnetic radiation, other parameters may also be selected to optimize the degree of crosslinking. For example, higher dosage and energy levels of radiation will typically result in a higher degree of crosslinking; however, it is generally desired that the materials not be "overexposed" to radiation. Such overexposure may result in an unwanted level of product degradation. Thus, in some embodiments, the total dosage employed (in one or multiple steps) may range from about 1 megarad (Mrad) to about 30 Mrads, in some embodiments, from about 3 Mrads to about 25 Mrads, and in some embodiments, from about 5 to about 15 Mrads. In addition, the energy level may range from about 0.05 megaelectron volts (MeV) to about 600 MeV.

It should be understood, however, that the actual dosage and/or energy level required depends on the type of polymers and electromagnetic radiation. Specifically, certain types of polymers may tend to form a lesser or greater number of crosslinks, which will influence the dosage and energy of the radiation utilized. Likewise, certain types of electromagnetic radiation may be less effective in crosslinking the polymer, and thus may be utilized at a higher dosage and/or energy level. For instance, electromagnetic radiation that has a relatively high wavelength (lower frequency) may be less efficient in crosslinking the polymer than electromagnetic radiation having a relatively low wavelength (higher frequency). Accordingly, in such instances, the desired dosage and/or energy level may be increased to achieve the desired degree of crosslinking.

Upon crosslinking, a three-dimensional crosslinked network is formed that provides the material with elasticity in the machine direction, cross-machine direction, or both. In addition to forming a three-dimensional elastomer network, crosslinking may also provide a variety of other benefits. Lotions used to enhance skin care, for instance, may contain petroleum-based components and/or other components that are compatible with thermoplastics polymers. If the lotions come into sufficient contact with an elastic material, its performance may be significantly degraded. In this regard, the crosslinked block copolymers may exhibit improvement in lotion degradation resistance. Furthermore, certain types of crosslinking techniques (e.g., electron beam radiation) may generate sufficient heat to effectively "heat shrink" the elastic material and provide it with additional latent stretchability. A separate heat activation step may also be employed to further enhance the heat shrinkage performance of the elastic material. Such an additional heat activation step may occur before and/or after crosslinking.

Although not required, one or more nonwoven web facings may be laminated to the elastic material to reduce the coefficient of friction and enhance the cloth-like feel of its surface. The basis weight of the nonwoven web facing may generally vary, such as from about 5 grams per square meter ("gsm") to 120 gsm, in some embodiments from about 8 gsm to about 70 gsm, and in some embodiments, from about 10 gsm to about 35 gsm. When multiple nonwoven web facings, such materials may have the same or different basis weights.

Exemplary polymers for use in forming nonwoven web facings may include, for instance, polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. If desired, biodegradable polymers, such as those described above, may also be employed. Synthetic or natural cellulosic polymers may also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth. It should be noted that the polymer(s) may also contain other additives, such as processing aids or treatment compositions to impart desired properties to the fibers, residual amounts of solvents, pigments or colorants, and so forth.

Monocomponent and/or multicomponent fibers may be used to form the nonwoven web facing. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. Nos. 4,789,592 to Taniguchi et al. and 5,336,552 to Strack, et al., 5,108,820 to Kaneko, et al., 4,795,668 to Kruege, et al., 5,382,400 to Pike, et al., 5,336,552 to Strack, et al., and 6,200,669 to Marmon, et al., which are incorporated herein in their entirety by reference thereto for all purposes. Multicomponent fibers having various irregular shapes may also be formed, such as described in U.S. Pat. Nos. 5,277,976 to Hogle, et al., 5,162,074 to Hills, 5,466,410 to Hills, 5,069,970 to Largman, et al., and 5,057,368 to Largman, et al., which are incorporated herein in their entirety by reference thereto for all purposes.

Although any combination of polymers may be used, the polymers of the multicomponent fibers are typically made from thermoplastic materials with different glass transition or melting temperatures where a first component (e.g., sheath) melts at a temperature lower than a second component (e.g., core). Softening or melting of the first polymer component of the multicomponent fiber allows the multicomponent fibers to form a tacky skeletal structure, which upon cooling, stabilizes the fibrous structure. For example, the multicomponent fibers may have from about 5% to about 80%, and in some embodiments, from about 10% to about 60% by weight of the low melting polymer. Further, the multicomponent fibers may have from about 95% to about 20%, and in some embodiments, from about 90% to about 40%, by weight of the high melting polymer. Some examples of known sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del.

Fibers of any desired length may be employed, such as staple fibers, continuous fibers, etc. In one particular embodiment, for example, staple fibers may be used that have a fiber length in the range of from about 1 to about 150 millimeters, in some embodiments from about 5 to about 50 millimeters, in some embodiments from about 10 to about 40 millimeters, and in some embodiments, from about 10 to about 25 millimeters. Although not required, carding techniques may be employed to form fibrous layers with staple fibers as is well known in the art. For example, fibers may be formed into a carded web by placing bales of the fibers into a picker that separates the fibers. Next, the fibers are sent through a combing or carding unit that further breaks apart and aligns the fibers in the machine direction so as to form a machine direction-oriented fibrous nonwoven web. The carded web may then be bonded using known techniques to form a bonded carded nonwoven web.

If desired, the nonwoven web facing used to form the nonwoven composite may have a multi-layer structure. Suitable multi-layered materials may include, for instance, spunbond/meltblown/spunbond (SMS) laminates and spunbond/meltblown (SM) laminates. Various examples of suitable SMS laminates are described in U.S. Pat. Nos. 4,041,203 to Brock et al.; 5,213,881 to Timmons, et al.; 5,464,688 to Timmons, et al.; 4,374,888 to Bornslaeger; 5,169,706 to Collier, et al.; and 4,766,029 to Brock et al., which are incorporated herein in their entirety by reference thereto for all purposes. In addition, commercially available SMS laminates may be obtained from Kimberly-Clark Corporation under the designations Spunguard® and Evolution®.

Another example of a multi-layered structure is a spunbond web produced on a multiple spin bank machine in which a spin bank deposits fibers over a layer of fibers deposited from a previous spin bank. Such an individual spunbond nonwoven web may also be thought of as a multi-layered structure. In this situation, the various layers of deposited fibers in the nonwoven web may be the same, or they may be different in basis weight and/or in terms of the composition, type, size, level of crimp, and/or shape of the fibers produced. As another example, a single nonwoven web may be provided as two or more individually produced layers of a spunbond web, a carded web, etc., which have been bonded together to form the nonwoven web. These individually produced layers may differ in terms of production method, basis weight, composition, and fibers as discussed above.

A nonwoven web facing may also contain an additional fibrous component such that it is considered a composite. For example, a nonwoven web may be entangled with another fibrous component using any of a variety of entanglement techniques known in the art (e.g., hydraulic, air, mechanical, etc.). In one embodiment, the nonwoven web is integrally entangled with cellulosic fibers using hydraulic entanglement. A typical hydraulic entangling process utilizes high pressure jet streams of water to entangle fibers to form a highly entangled consolidated fibrous structure, e.g., a nonwoven web. Hydraulically entangled nonwoven webs of staple length and continuous fibers are disclosed, for example, in U.S. Pat. Nos. 3,494,821 to Evans and 4,144,370 to Boulton, which are incorporated herein in their entirety by reference thereto for all purposes. Hydraulically entangled composite nonwoven webs of a continuous fiber nonwoven web and a pulp layer are disclosed, for example, in U.S. Pat. Nos. 5,284,703 to Everhart, et al. and 6,315,864 to Anderson, et al., which are incorporated herein in their entirety by reference thereto for all purposes. The fibrous component of the composite may contain any desired amount of the resulting substrate. The fibrous component may contain greater than about 50% by weight of the composite, and in some embodiments, from about 60% to about 90% by weight of the composite. Likewise, the nonwoven web may contain less than about 50% by weight of the composite, and in some embodiments, from about 10% to about 40% by weight of the composite.

The nonwoven web facing may be necked in one or more directions prior to lamination to the film of the present invention. Suitable necking techniques are described in U.S. Pat. Nos. 5,336,545, 5,226,992, 4,981,747 and 4,965,122 to Morman, as well as U.S. Patent Application Publication No. 2004/0121687 to Morman, et al. Alternatively, the nonwoven web may remain relatively inextensible in a direction prior to lamination to the film. In such embodiments, the nonwoven web may be optionally stretched in one or more directions subsequent to lamination to the elastic material.

Any of a variety of techniques may be employed to laminate the layers together, including adhesive bonding; thermal bonding; ultrasonic bonding; microwave bonding; extrusion coating; and so forth. In one particular embodiment, nip rolls apply a pressure to the precursor elastic material (e.g., film) and nonwoven facing(s) to thermally bond the materials together. The rolls may be smooth and/or contain a plurality of raised bonding elements. Adhesives may also be employed, such as Rextac 2730 and 2723 available from Huntsman Polymers of Houston, Tex., as well as adhesives available from Bostik Findley, Inc, of Wauwatosa, Wis. The type and basis weight of the adhesive used will be determined on the elastic attributes desired in the final composite and end use. For instance, the basis weight of the adhesive may be from about 1.0 to about 3.0 gsm. The adhesive may be applied to the nonwoven web facings and/or the elastic material prior to lamination using any known technique, such as slot or melt spray adhesive systems. During lamination, the elastic material may in a stretched or relaxed condition depending on the desired properties of the resulting composite.

The lamination of the nonwoven web facing(s) and elastic material(s) may occur before and/or after crosslinking of the block copolymer. In one embodiment, for example, a precursor elastic material is initially laminated to a nonwoven web facing, and the resulting composite is subsequently subjected to electromagnetic radiation of a certain dosage. FIG. 1 schematically illustrates an exemplary process 10 for forming a stretch-bonded composite in this manner. Initially, a thermoplastic precursor layer 126 is stretched between a first set of nip rolls 132 and 134, and a second set of nip rollers 136 and 138. To induce stretching, the second set of nip rolls may turn at a surface speed faster than the first set of nip rolls. Nonwoven facing layers 24 and 28 are also unwound from storage rolls 26 and 30 and combined with the stretched precursor layer 126 to form a composite 40 between nip rolls 136 and 138, while the nonwoven layers 24 and 28 are relaxed. The layers may be combined with the aid of an adhesive applied to the nonwoven layers or the precursor layer, or with the aid of heat supplied from roll 136 and/or 138.

After the composite 40 is formed, it then passes through a crosslinking station 128, thereby forming a composite that may be wound onto a roll 44. The composite may be elastic in the machine direction, cross-machine direction, or both. Although not shown, various additional potential processing and/or finishing steps known in the art, such as slitting, treating, printing graphics, etc., may be performed without departing from the spirit and scope of the invention. For instance, the composite may optionally be mechanically stretched in the cross-machine and/or machine directions to enhance extensibility. In one embodiment, the composite may be coursed through two or more rolls that have grooves in the CD and/or MD directions. Such grooved satellite/anvil roll arrangements are described in U.S. Patent Application Publication Nos. 2004/0110442 to Rhim, et al. and 2006/0151914 to Gerndt, et al., which are incorporated herein in their entirety by reference thereto for all purposes. For instance, the composite may be coursed through two or more rolls that have grooves in the CD and/or MD directions. The grooved rolls may be constructed of steel or other hard material (such as a hard rubber). If desired, heat may be applied by any suitable method known in the art, such as heated air, infrared heaters, heated nipped rolls, or partial wrapping of the composite around one or more heated rolls or steam canisters, etc. Heat may also be applied to the grooved rolls themselves. It should also be understood that other grooved roll arrangement are equally suitable, such as two grooved rolls positioned immediately adjacent to one another. Besides grooved rolls, other techniques may also be used to mechanically stretch the composite in one or more directions. For example, the composite may be passed through a tenter frame that stretches the composite. Such tenter frames are well known in the art and described, for instance, in U.S. Patent Application Publication No. 2004/0121687 to Morman, et al. The composite may also be necked. Suitable techniques necking techniques are described in U.S. Pat. Nos. 5,336,545, 5,226,992, 4,981,747 and 4,965,122 to Morman, as well as U.S. Patent Application Publication No. 2004/0121687 to Morman, et al., all of which are incorporated herein in their entirety by reference thereto for all purposes.

The elastic material of the present invention may have a wide variety of applications, but is particularly useful as a component of an absorbent article. Although not required, a precursor elastic material may be incorporated into the absorbent article and subsequently crosslinked. In this manner, the material is not highly elastic prior to crosslinking and is thus more dimensionally stable than highly elastic materials. This decreases the need for maintaining the material in a mechanically stretched condition during attachment to other components of the absorbent article and thus provides greater freedom in the location and manner in which the components are attached together. Of course, the precursor elastic material may also be crosslinked prior to incorporation into the absorbent article, such as described above and illustrated in FIG. 1.

Figure 2:
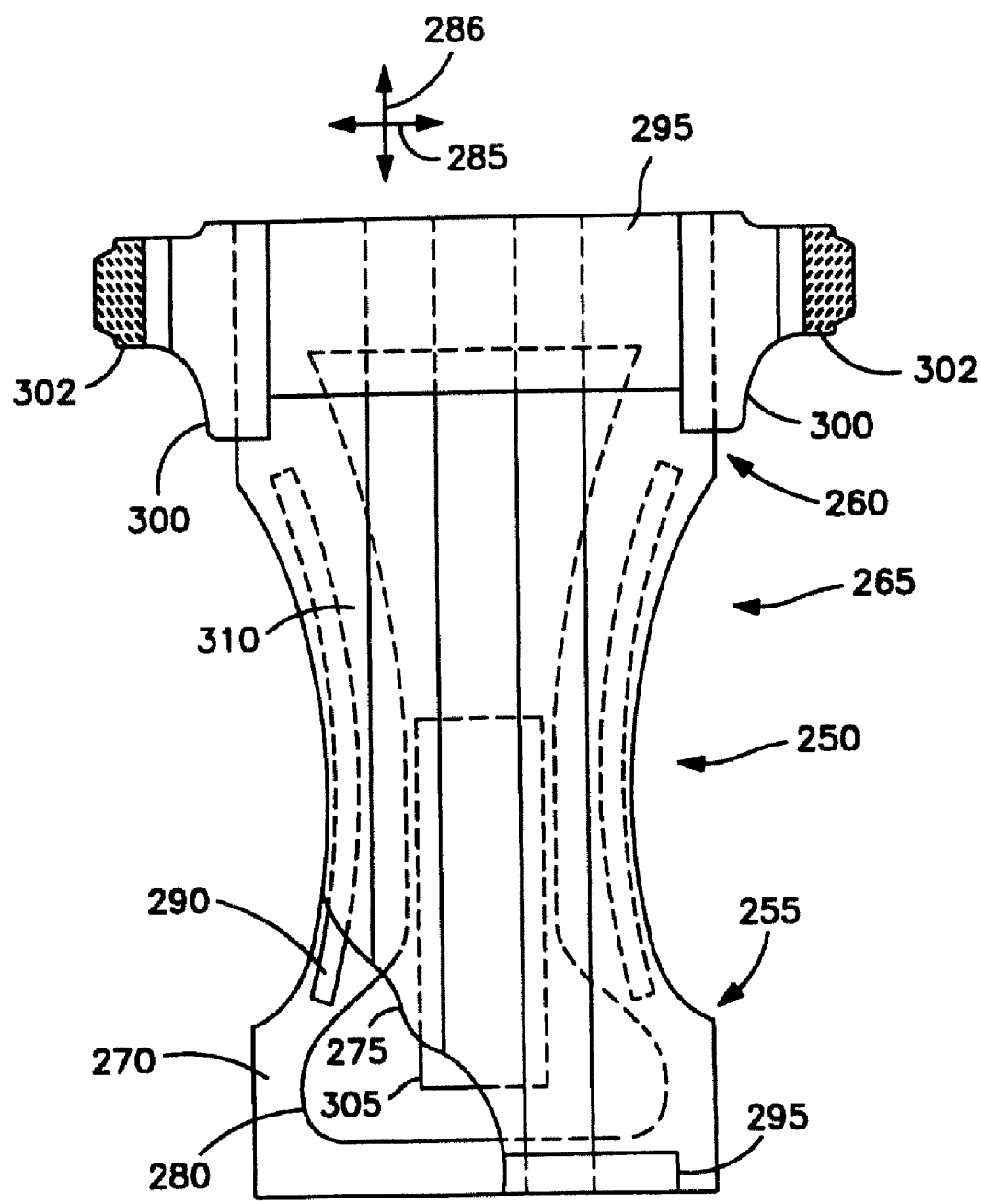
FIG. 2 is a perspective view of an absorbent article that may be formed in accordance with one embodiment of the present invention.

The absorbent article normally includes a substantially liquid-impermeable layer (e.g., outer cover), a liquid-permeable layer (e.g., bodyside liner, surge layer, etc.), an absorbent core, and various other optional components. As is well known in the art, a variety of absorbent article components may possess elastic characteristics, such as waistbands, leg/cuff gasketing, ears, side panels, outer covers, and so forth. The crosslinked elastic material of the present invention may be employed for use in any of such components. Referring to FIG. 2, for example, one embodiment of a disposable diaper 250 is shown that generally defines a front waist section 255, a rear waist section 260, and an intermediate section 265 that interconnects the front and rear waist sections. The front and rear waist sections 255 and 260 include the general portions of the diaper which are constructed to extend substantially over the wearer's front and rear abdominal regions, respectively, during use. The intermediate section 265 of the diaper includes the general portion of the diaper that is constructed to extend through the wearer's crotch region between the legs. Thus, the intermediate section 265 is an area where repeated liquid surges typically occur in the diaper.

The diaper 250 includes, without limitation, an outer cover, or backsheet 270, a liquid permeable bodyside liner, or topsheet, 275 positioned in facing relation with the backsheet 270, and an absorbent core body, or liquid retention structure, 280, such as an absorbent pad, which is located between the backsheet 270 and the topsheet 275. The backsheet 270 defines a length, or longitudinal direction 286, and a width, or lateral direction 285 which, in the illustrated embodiment, coincide with the length and width of the diaper 250. The liquid retention structure 280 generally has a length and width that are less than the length and width of the backsheet 270, respectively. Thus, marginal portions of the diaper 250, such as marginal sections of the backsheet 270 may extend past the terminal edges of the liquid retention structure 280. In the illustrated embodiments, for example, the backsheet 270 extends outwardly beyond the terminal marginal edges of the liquid retention structure 280 to form side margins and end margins of the diaper 250. The topsheet 275 is generally coextensive with the backsheet 270 but may optionally cover an area that is larger or smaller than the area of the backsheet 270, as desired.

To provide improved fit and to help reduce leakage of body exudates from the diaper 250, the diaper side margins and end margins may be elasticized with suitable elastic members, as further explained below. For example, as representatively illustrated in FIG. 2, the diaper 250 may include leg/cuff gasketing 290 constructed to operably tension the side margins of the diaper 250 and closely fit around the legs of the wearer to reduce leakage and provide improved comfort and appearance. Waistbands 295 are employed that provide a resilient, comfortably close fit around the waist of the wearer. The crosslinked elastic material of the present invention is suitable for use as the leg/cuff gasketing 290 and/or waistbands 295. Exemplary of such materials are composite sheets that either comprise or are adhered to the backsheet, such that elastic constrictive forces are imparted to the backsheet 270.

As is known, fastening means, such as hook and loop fasteners, may be employed to secure the diaper 250 on a wearer. Alternatively, other fastening means, such as buttons, pins, snaps, adhesive tape fasteners, cohesives, fabric-and-loop fasteners, or the like, may be employed. In the illustrated embodiment, the diaper 250 includes a pair of side panels 300 (or ears) to which the fasteners 302, indicated as the hook portion of a hook and loop fastener, are attached. Generally, the side panels 300 are attached to the side edges of the diaper in one of the waist sections 255, 260 and extend laterally outward therefrom. The side panels 300 may contain the elastic material of the present invention. Examples of absorbent articles that include side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

The diaper 250 may also include a surge management layer 305, located between the topsheet 275 and the liquid retention structure 280, to rapidly accept fluid exudates and distribute the fluid exudates to the liquid retention structure 280 within the diaper 250. The diaper 250 may further include a ventilation layer (not illustrated), also called a spacer, or spacer layer, located between the liquid retention structure 280 and the backsheet 270 to insulate the backsheet 270 from the liquid retention structure 280 to reduce the dampness of the garment at the exterior surface of a breathable outer cover, or backsheet, 270. Examples of suitable surge management layers 305 are described in U.S. Pat. No. 5,486,166 to Bishop and U.S. Pat. No. 5,490,846 to Ellis.

As representatively illustrated in FIG. 2, the disposable diaper 250 may also include a pair of containment flaps 310 which are configured to provide a barrier to the lateral flow of body exudates. The containment flaps 310 may be located along the laterally opposed side edges of the diaper adjacent the side edges of the liquid retention structure 280. Each containment flap 310 typically defines an unattached edge that is configured to maintain an upright, perpendicular configuration in at least the intermediate section 265 of the diaper 250 to form a seal against the wearer's body. The containment flaps 310 may extend longitudinally along the entire length of the liquid retention structure 280 or may only extend partially along the length of the liquid retention structure. When the containment flaps 310 are shorter in length than the liquid retention structure 280, the containment flaps 310 can be selectively positioned anywhere along the side edges of the diaper 250 in the intermediate section 265. Such containment flaps 310 are generally well known to those skilled in the art. For example, suitable constructions and arrangements for containment flaps 310 are described in U.S. Pat. No. 4,704,116 to Enloe.

The diaper 250 may be of various suitable shapes. For example, the diaper may have an overall rectangular shape, T-shape or an approximately hour-glass shape. In the shown embodiment, the diaper 250 has a generally I-shape. Other suitable components which may be incorporated on absorbent articles of the present invention may include waist flaps and the like which are generally known to those skilled in the art. Examples of diaper configurations suitable for use in connection with the elastic materials of the present invention that may include other components suitable for use on diapers are described in U.S. Pat. Nos. 4,798,603 to Meyer, et al.; 5,176,668 to Bernardin; 5,176,672 to Bruemmer, et al.; 5,192,606 to Proxmire, et al.; and 5,509,915 to Hanson, et al., which are incorporated herein in their entirety by reference thereto for all purposes.

The various regions and/or components of the diaper 250 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the topsheet 275 and backsheet 270 may be assembled to each other and to the liquid retention structure 280 with lines of adhesive, such as a hot melt, pressure-sensitive adhesive. Similarly, other diaper components, such as the leg/cuff gasketing 290, waistband 295, fastening members 302, and surge layer 305 may be assembled into the article by employing the above-identified attachment mechanisms.

Although various configurations of a diaper have been described above, it should be understood that other diaper and absorbent article configurations are also included within the scope of the present invention. In addition, the present invention is by no means limited to diapers. In fact, any other absorbent article may be formed in accordance with the present invention, including, but not limited to, other personal care absorbent articles, such as training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth. Several examples of such absorbent articles are described in U.S. Pat. Nos. 5,649,916 to DiPalma, et al.; 6,110,158 to Kielpikowski; 6,663,611 to Blaney, et al., which are incorporated herein in their entirety by reference thereto for all purposes. Still other suitable articles are described in U.S. Patent Application Publication No. 2004/0060112 A1 to Fell et al., as well as U.S. Pat. Nos. 4,886,512 to Damico et al.; 5,558,659 to Sherrod et al.; 6,888,044 to Fell et al.; and 6,511,465 to Freiburger et al., all of which are incorporated herein in their entirety by reference thereto for all purposes. Of course, the elastic material is versatile and may also be incorporated into a wide variety of other types of articles. For example, the elastic material may be incorporated into a medical garment, such as gowns, caps, drapes, gloves, facemasks, etc.; industrial workwear garment, such as laboratory coats, coveralls, etc.; and so forth.

The present invention may be better understood with reference to the following prophetic example.

Test Methods

Cycle Testing

The materials may be tested using a cyclical testing procedure to determine load loss and percent set. For example, 1-cycle testing may be utilized to 200% defined elongation. For this test, the sample size may be 3 inches in the cross-machine direction by 6 inches in the machine direction. The grip size may be 3 inches in width. The grip separation may be 4.5 inches. The samples may be loaded such that the machine direction of the sample is in the vertical direction. A preload of approximately 10 to 15 grams may be set. The test may pull the sample to 200% elongation at a speed of 20 inches per minute, and then immediately (without pause) return to zero at a speed of 20 inches per minute. The test reports percent set and percent hysteresis. The "percent set" is the measure of the amount of the material stretched from its original length after being cycled (the immediate deformation following the cycle test). The percent set is where the retraction curve of a cycle crosses the elongation axis. The remaining strain after the removal of the applied stress may be measured as the percent set. The hysteresis value is the loss of energy during the cyclic loading. The testing may be done on a MTS Corp. constant rate of extension tester 2/S with a Renew MTS mongoose box (controller) using TESTWORKS 4.07b software (MTS Corp, of Minneapolis, Minn.). The tests may be conducted at ambient conditions.

Stress Relaxation

Stress relaxation is defined as the force required to hold a given elongation constant over a period of time and is generally indicative of the dimensional stability of a material. Testing may be performed by clamping a test specimen (3" in width) between the jaws of a MTS extension tester at a 3" grip to grip distance. The sample and the grip fixtures may be enclosed in an environmental chamber. The sample, after clamping, may be equilibrated at 100° F. for 3 minutes. The sample may then be elongated to a final constant elongation of 4.5 inches (50% elongation) at a cross-head displacement speed of 20 inches per minute. The load required to maintain the 50% elongation as a function of time may be monitored. The slope of the stress curve and the percent load loss may be reported. The percent load loss may be calculated by subtracting the load at 12 hours from the initial load, dividing by the initial load, and then multiplying the ratio by 100. The slope, which is constant over the time period, is determined from a plot of log (load) versus log (time), or from the following equation:

$$m = \frac{-\Delta \log[(L(t)/L(0)]}{\Delta \log t}$$

wherein, m=the slope,

L(t)=load at a given time (t),

L(0)=starting load at t=0, and t=time.

The testing may be done on a MTS Corp. constant rate of extension tester 2/S with a Renew MTS mongoose box (controller) using TESTWORKS 4.07b software (MTS Corp, of Minneapolis, Minn.).

Prophetic Example

A polymer blend may be formed from 90 wt. % of a radial B-S-B block copolymer and 10 wt. % of ESCOREZ® 5600 (Exxon Mobil Chemical Co.). The B-S-B block copolymer may have a styrene content of 20 wt. %. ESCOREZ® 5600 is a hydrocarbon resin. The blend may be introduced into the hopper of a Leistritz twin screw co-rotating multi-mode extruder (Model Mic 27GL/40D) equipped with 27 mm screws at a 40:1 length:diameter ratio ("L/D"). The extruder may be an electrical resistance heated extruder with water cooling, and contain 9 barrel heating sections and 2 auxiliary heating sections. The extruder may be fitted with two "pineapple" mixing elements based on the principle of distributive mixing in the middle and end zones. The extruder may also be directly fitted with a 10" coat-hanger type film die that can be heated. Exemplary extrusion parameters are set forth below in Table 1:

TABLE 1

Extrusion Parameters

| | Sample | |
|---|---|---|
| | 1 | 2 |
| Feed Rate (lb/hr) | 8 | 8 |
| Screw Speed (rpms) | 300 | 300 |
| Zone 1 (° C.) | 150 | 150 |
| Zone 2 (° C.) | 150 | 150 |
| Zone 3 (° C.) | 160 | 160 |
| Zone 4 (° C.) | 160 | 160 |
| Zone 5 (° C.) | 160 | 160 |
| Zone 6 (° C.) | 160 | 160 |
| Zone 7 (° C.) | 160 | 160 |
| Zone 8 (° C.) | 160 | 160 |
| Zone 9 (° C.) | 160 | 160 |
| Zone 10 (° C.) | 160 | 160 |
| Zone 11 (° C.) | 160 | 160 |
| Torque (lbs) | 29 | 30 |
| Winder Speed (ft/min) | 8 | 13 |
| Die Pressure (psi) | 700 | 710 |

Once formed, the film samples may be subjected to electron beam radiation using Energy Sciences' pilot line equipment, which may be operated at a voltage range from 80 kV to 200 kV, at a depth of 150 microns, density of 1 g/cc, and a dosage range of 1-9 Mrads depending on speed. The samples may have an approximate dimension of 10"×11" and may be placed on a carrier film that unwinds at one end and winds in the other end. Exposed samples may be collected and run a second or third time depending on the dosage required. The materials may be tested for elastomeric performance as described above.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A nonwoven web material comprising an elastic component that includes a crosslinked elastomeric network containing a branched block copolymer having a monoalkenyl aromatic midblock positioned between conjugated diene endblocks.

2. The nonwoven web material of claim 1, wherein the monoalkenyl aromatic midblock includes styrene or a derivative thereof and the conjugated diene endblocks include butadiene, isoprene, or a mixture thereof.

3. The nonwoven web material of claim 1, wherein the copolymer is a triblock copolymer.

4. The nonwoven web material of claim 1, wherein the copolymer constitutes about 10 wt. % or more of the elastic material.

5. The nonwoven web material of claim 1, wherein the copolymer constitutes about 50 wt. % or more of the elastic material.

6. The nonwoven web material of claim 1, wherein the material is a composite that contains a nonwoven web facing laminated to the elastic component.

7. The nonwoven web material of claim 6, wherein the elastic component is a film, strands, web, or a combination thereof.

8. The nonwoven web material of claim 1, wherein the branched block copolymer contains arms that extend radially from a branch point.

9. The nonwoven web material of claim 8, wherein the branched block copolymer contains from about 3 to about 30 arms.

10. An absorbent article comprising an absorbent core positioned between a substantially liquid-impermeable layer and a liquid-permeable layer, the absorbent article comprising the nonwoven web material of claim 1.

11. A method for forming a nonwoven composite, the method comprising:
melt extruding a branched block copolymer having a monoalkenyl aromatic midblock positioned between conjugated diene endblocks;
forming a precursor elastic material from the melt extruded copolymer;
laminating the precursor elastic material to a nonwoven web facing; and
crosslinking the branched block copolymer to form a crosslinked elastomeric network.

12. The method of claim 11, wherein the precursor elastic material includes a film, strands, web, or a combination thereof.

13. The method of claim 11, wherein the laminating occurs prior to crosslinking of the branched block copolymer.

14. The method of claim 11, wherein the laminating occurs after crosslinking of the branched block copolymer.

15. The method of claim 11, wherein crosslinking is induced by electromagnetic radiation.

16. The method of claim 15, wherein the electromagnetic radiation has a wavelength of about 100 nanometers or less.

17. The method of claim 15, wherein the dosage of the electromagnetic radiation is from about 1 to about 30 Megarads.

18. The method of claim 15, wherein the dosage of the electromagnetic radiation is from about 5 to about 15 Megarads.

19. The method of claim 11, wherein the monoalkenyl aromatic midblock includes styrene or a derivative thereof and the conjugated diene endblocks include butadiene, isoprene, or a mixture thereof.

20. The method of claim 11, wherein the copolymer is a triblock copolymer.

21. The method of claim 11, wherein the branched block copolymer contains arms that extend radially from a branch point.

22. The method of claim 21, wherein the branched block copolymer contains from about 3 to about 30 arms.

23. The nonwoven web material of claim 1, wherein the monoalkenyl aromatic midblock constitutes from about 1 wt. % to about 40 wt. % of the copolymer.

24. The nonwoven web material of claim 1, wherein the monoalkenyl aromatic midblock constitutes from about 15 wt. % to about 35 wt. % of the copolymer.

* * * * *